United States Patent [19]
Rubinstein

[11] Patent Number: 5,211,912
[45] Date of Patent: * May 18, 1993

[54] METHOD FOR DISINFECTING RED BLOOD CELLS, BLOOD PRODUCTS, AND CORNEAS

[75] Inventor: Alan I. Rubinstein, Los Angeles, Calif.

[73] Assignee: University of Southern California, Los Angeles, Calif.

[ * ] Notice: The portion of the term of this patent subsequent to Nov. 20, 2007 has been disclaimed.

[21] Appl. No.: 556,756

[22] Filed: Jul. 23, 1990

Related U.S. Application Data

[63] Continuation-in-part of Ser. No. 492,723, Mar. 13, 1990, Continuation-in-part of Ser. No. 230,839, Aug. 9, 1988, Pat. No. 4,971,760, Continuation-in-part of Ser. No. 892,058, Sep. 1, 1986, abandoned, which is a continuation-in-part of Ser. No. 838,253, Mar. 10, 1986, abandoned.

[51] Int. Cl.$^5$ .......... A61K 35/16; A61L 2/18; A61L 2/20; C07K 15/06
[52] U.S. Cl. .......... 422/37; 422/28; 424/661; 435/2; 530/412
[58] Field of Search .......... 422/28, 37; 435/2; 530/412; 424/661

[56] References Cited

U.S. PATENT DOCUMENTS

| | | |
|---|---|---|
| Re. 27,359 | 5/1972 | Ilg . |
| Re. 31,779 | 12/1984 | Alliger .......... 422/28 X |
| 3,031,378 | 4/1962 | Ishidate . |
| 3,100,737 | 8/1963 | Auerswald . |
| 4,314,997 | 2/1982 | Shanbrom . |
| 4,481,189 | 11/1984 | Prince . |
| 4,632,980 | 12/1986 | Zee et al. .......... 530/380 |
| 4,675,159 | 6/1987 | Al-Sioufe .......... 422/36 |
| 4,833,165 | 5/1989 | Louderback .......... 422/36 X |
| 4,944,920 | 7/1990 | Rubinstein .......... 435/2 X |
| 4,971,760 | 11/1990 | Rubinstein .......... 435/2 X |
| 5,019,402 | 5/1991 | Kross et al. .......... 435/2 X |

OTHER PUBLICATIONS

Spire, et al., The Lancet, Oct. 20, 1984, pp. 899–901.
Sarin, et al., The New England Journal of Medicine, Nov. 28, 1985, p. 1416.

*Primary Examiner*—Jill A. Johnston
*Attorney, Agent, or Firm*—Poms, Smith, Lande & Rose

[57] ABSTRACT

A method to inactivate viruses or to disinfect blood products, for instance units of red blood cells, wherein a disinfectant or virus inactivating chemical is made isotonic or nearly isotonic, and wherein the red blood cells are exposed to isotonic disinfectant to inactivate any agent which may be present, for example HIV-1 virus which causes AIDS. The method may also be applied to plasma fractions and corneas.

32 Claims, No Drawings

METHOD FOR DISINFECTING RED BLOOD CELLS, BLOOD PRODUCTS, AND CORNEAS

RELATED APPLICATIONS

This is a continuation-in-part of U.S. patent application Ser. No. 492,723, filed Mar. 13, 1990; which in turn is a continuation-in-part of Ser. No. 230,839, filed Aug. 9, 1988 and now U.S. Pat. No. 4,971,760; which in turn was a continuation-in-art of Ser. No. 892,058, filed Sep. 1, 1986 and now abandoned; which in turn was a continuation-in-part of Ser. No. 838,253, filed Mar. 10, 1986 and now abandoned.

BACKGROUND

1. Field of the Invention

The present invention relates generally to processing human blood products, i.e., whole blood, red blood cells, blood plasma and blood proteins. Additionally, it relates to processing human and animal tissue, e.g., organs and parts of organs used in transplants. More particularly, this invention relates to disinfecting certain blood products and corneas so that they may be used safely and effectively for diagnostic, therapeutic or research purposes.

2. Description of the Related Art

Blood products from human and animal donors are widely used for therapeutic, diagnostic and experimental purposes. Such blood products are subject to contamination by several blood-borne viruses and other micro-organisms. There has been no way to assure that the recipients of blood products or those who handle the products are free from potential exposure to viruses. In particular, the transfusion of human blood products carries a well-known risk of transmitting a number of viruses.

Of particular threat are viruses that appear to cause various forms of hepatitis, including the hepatitis B virus; the non-A, non-B hepatitis virus or viruses. Others of interest are cytomegalovirus and Epstein-Barr virus.

Viruses linked with the incurable and often fatal disease known as acquired immune deficiency syndrome or "AIDS" are probably caused by a retrovirus or group of retroviruses previously denominated "HTLV-III" and other HTLV types—and more currently "HIV" "HIV-1" and "HIV-2." The most common cause of AIDS is thought to be HTLV-III, now usually called HIV-1.

Detection and isolation of such cytopathic retroviruses from patients with AIDS, and certain members of groups that are at high risk for AIDS, have been frequently reported. One such report appears in *Science* 224:500–03 (1984).

Such findings are corroborated by P. S. Savin, et al., in an article entitled "Human T-Lymphotrophic Retroviruses in Adult T-cell Leukemia-Lymphoma and Acquired Immune Deficiency Syndrome," *J. Clinical Immunol.* 4:415–23 (1984). Yet another report is by F. Wong-Staal and R. C. Gallo, "Human T-Lymphotrophic Retroviruses," *Nature* 317:395–402 (1985).

While the hazard of hepatitis and AIDS transmission through transfusion of blood products has received great public attention, the analogous hazard of such transmission through transplantation tissues is a much less familiar matter. Nevertheless, there is a recognized possibility of at least AIDS virus transmission from corneal transplantation, according to *Corneal Surgery Theory, Technique and Tissue*, F. S. Brightbill, ed., p. 53 (Mosby 1986).

Furthermore, contamination of corneas by bacteria and fungi is documented, id. at 52, even though antibacterial solutions are commonly used in pre-transplant storage of corneas—generally within the nutrient medium that supports the corneas.

Disinfecting blood products and tissue products with disinfectants strong enough to significantly inactivate viruses has generally been discounted because they damage cellular blood constituents, and any residual disinfectant in the blood product to be transfused could be hazardous to the recipient of the transfusion.

One disinfectant in use for blood products is beta-propiolactone. Beta-propiolactone, however, is a known carcinogen and hence potentially very dangerous. To the extent that significant residual quantities of this material may remain in the blood product which is actually transfused, the use of propiolactone represents a significant hazard.

U.S. Pat. No. 4,833,165 relates to using as little as 0.1% formaldehyde and/or phenol to inactivate HTLV-III in blood. However, recently available data and information indicate that red blood cells treated with as little as 0.02% formaldehyde and 0.01% phenol are not viable and not suitable for transfusion.

A variety of disinfectants have been used in the medical profession and biomedical industry to disinfect work areas, table tops, walls, surgical instruments, etc., for the purpose of inactivating viruses and micro-organisms associated with blood and tissue products. In particular, U.S. Pat. No. Re. 31,779 relates to the effective use of materials which liberate chlorine dioxide for such purposes. Other compositions which are known in the medical profession to be useful for sterilizing and disinfecting work areas and tools are lower alkyl monohydric alcohols, aldehydes, mineral acids and bases, peroxides, sodium hypochlorite, quaternary ammonium salts and iodine containing compounds. None of these disinfectants have been applied to disinfecting blood products or tissue products. Such compositions in contact with blood and tissue products would cause one to expect resulting damage to the cells and tissue.

Accordingly, there presently is a need to provide a method to disinfect human and animal blood products and human and animal tissue products. In particular, there is a need to disinfect such products so that they can be safely and effectively utilized by a recipient or handled by a user without exposure to harmful viruses and micro-organisms.

SUMMARY OF THE DISCLOSURE

It is the object of this invention to provide a composition and method to disinfect blood products and tissue products for their safe and effective use. The invention is based upon the surprising and unexpected discovery that some disinfecting compounds, which heretofore have been discounted as disinfectants for blood products or tissue products, may be used for disinfecting blood products without lysing or otherwise damaging blood cells and tissue cells.

The foregoing object of the present invention is accomplished by combining a particular disinfectant with a diluent in which the disinfectant is soluble to form a disinfectant composition which is isotonic with blood. Surprisingly such a solution will not only disinfect blood products but will do so without damage to the blood product, e.g., blood cells, and tissue cells. Such compositions may be used for therapeutic or diagnostic purposes following the disinfectant procedure.

It is presently believed that the disinfectant compositions of the present invention will render blood products, e.g., blood cells, safe, i.e., inactivate harmful viruses and virus-like agents present in blood products. As noted, this is accomplished by using certain disinfectant compositions which will not harm the blood products or tissue products, e.g., cause hemolysis of red blood cells. Such disinfectant compositions consists of a suitable disinfectant and an aqueous diluent. The aqueous diluent consists of a solute which when it is at the proper concentration, the disinfectant composition is substantially isotonic with blood. The disinfectant is preferably sodium chlorite and at least one acid, chlorine dioxide, or a water soluble chlorine dioxide liberating compound. Chlorine dioxide disinfectants and those compounds which form chlorine dioxide in situ such as sodium chlorite and an acid are described with further detail in U.S. Pat. No. Re. 31,779 issued to Alliger. This disclosure is hereby incorporated by reference in the present application for patent.

Solutes which, when dissolved in water at a proper concentration form isotonic solutions, are known in the art and therefore no detailed description thereof is necessary. Exemplary solutes which are useful in the present invention include sugars such as dextrose, CPD (citrate phosphate dextrose), CPDA-1 (citrate-phosphate-dextrose-adenine), dextran, albumin, alkaline earth metal halides (preferably chlorides) such as calcium chloride, magnesium bromide and calcium fluoride, and alkali metal halide (preferably chlorine) such as sodium chloride potassium bromide.

It is, of course, understood that if red blood cells are to be disinfected, the disinfectant composition must be isotonic to red blood cells. This is particularly applicable when the disinfectant system itself exerts an osmotic gradient. Thus, a higher concentration of sodium chlorite and an acid can be diluted in a solution which is slightly hypotonic with respect to red blood cells. For small concentrations of disinfectant, the diluent solution will itself be isotonic, e.g., 0.9% saline or normal saline. The controlling factor is that the disinfectant composition exert an osmotic pressure which is substantially enough to prevent hemolysis.

This invention may be practiced using economical procedures which are easily adapted to existing handling techniques for blood products and tissue products. For blood products, this invention can be implemented even while the blood product is in a collection bag. For corneas (or parts thereof), the method can be implemented with only minor, non-disruptive departure from familiar surgical protocols.

In general, the method of this invention consists of washing the cellular blood constituent, plasma or platelets, or tissue in an isotonic solution of disinfectant. An important limitation in choosing the isotonic medium is that it must be compatible and non-reactive.

The disinfectant concentration and the time required to effectively inactivate any harmful substance is dependent upon the disinfectant strength. Suitable concentrations and disinfecting times will become evident in the more detailed description of the invention and the exemplary embodiments.

After washing the cellular blood constituent, plasma or platelets, or tissue, the disinfectant is separated from the disinfecting composition. The separation is accomplished by washing the disinfected composition in a medium which is isotonic solution with blood until the disinfectant is reduced to a safe or insignificant level. Preferably the medium is the same as that used to disinfect the blood or tissue product.

Further objects, features, and advantages of the present invention will become apparent to those skilled in the art from a consideration of the following detailed description.

DETAILED DESCRIPTION OF THE PREFERRED EMBODIMENT

The present invention involves the effective and safe disinfection of blood products and tissue products. The invention has wide application to all blood products such as whole blood for transfusion, blood cells, blood plasma and blood proteins. It is also suitable for disinfecting tissue products such as corneas intended for transplant from a donor to a recipient.

In accordance with the preferred method for disinfecting blood products, a method is provided in which viruses, including the HIV viruses, in blood products and tissue products are inactivated. Additionally, the disinfected blood products, and tissue products may be used subsequently for therapeutic or diagnostic purposes in a safe and effective manner. The invention is based upon the unexpected discovery that disinfectant compositions which are substantially isotonic with blood do not lyse red blood cells or tissue cells or cause harm to blood products.

The method of the present invention consists of mixing blood products, or tissue products with a disinfectant composition for a sufficient time to inactivate viruses present. The disinfectant composition consists of a disinfectant and a diluent. The disinfectant is preferably sodium chlorite and at least one acid, chlorine dioxide, or a water soluble chlorine dioxide liberating compound. The aqueous diluent consists of a solute which, when it is at the proper concentration, the disinfectant composition is substantially isotonic with blood. The method further consists of separating the disinfectant from the blood product or tissue product, providing a product which is viable for diagnostic or therapeutic use.

Acids which are suitable for use in the disinfectant compositions utilized in the methods of the present invention are both organic and inorganic acids which are capable of reacting with sodium chlorite and other water soluble chlorine dioxide liberating compounds to produce chlorine dioxide. Organic carboxylic acids are particularly useful and include but are not limited to such acids as lactic acid, acetic acid, citric acid, pyruvic acid, sorbic acid, succinic acid and fumaric acid. Additionally, inorganic acids such as hydrochloric acid, sulfuric acid, and phosphoric acid can be utilized in the disinfectant composition.

In accordance with the present invention solutes suitable for use in the diluent can be chosen from any of a number of compounds used in the preparation of isotonic solutions. Such solutes include but are not limited to saline or sodium chloride, dextrose, glucose, dextrans, and albumin, as well as salts of alkali earth metals. Combinations of solutes which are frequently utilized in storing physiological cells in tissue are also suitable. Exemplary combination of solutes include citrate-phosphate-dextrose, citrate-phosphate-dextrose-adenine, and saline-mannitol-dextrose-adenine.

Solute concentrations, disinfectant concentrations, and suitable disinfecting times are dependent upon the nature of the disinfectant which is used in the procedure. However, appropriate solute concentrations are dependent upon the disinfectant concentrations. As mentioned above, when the solute is at the proper concentration, the disinfectant composition is substantially isotonic with blood. Thus, when a disinfectant composition consists of less than 0.001% sodium chlorite and less than 0.005% acid there is very little if any osmotic pressure exerted by the disinfectant. In such a case, the diluent itself is isotonic and may be normal saline or 5% glucose, among other possible diluents.

On the other hand, when the disinfectant is much more concentrated and the disinfectant composition consists of up to 0.25% sodium chlorite and up to 0.2% acid, the diluent may be 0.45% saline. This is possible because the higher concentrations of disinfectant and acid exert an osmotic pressure themselves. It is primarily controlling that the disinfectant composition exert an osmotic pressure which is substantially high enough to prevent hemolysis.

Although it is not necessary for the practice of the present invention, the separation step preferentially is performed using an automated cell washer or semi-automated cell washer. Additionally, it is preferential to wash the blood product and tissue product with a solution which is isotonic. This practice, provides additional assurance that the tissue and cells are not harmed during the separating and washing procedure. It is further preferable that the washing procedure is practiced until the concentration of disinfectant in the tissue product or blood product is insignificant.

In a case where the blood proteins are of interest, the disinfectant separation step advantageously includes precipitating out the plasma proteins in a generally conventional fashion. Preferably this precipitation is produced by contact with ammonium sulfate or like precipitating agent, generally at a concentration of 80% or less.

The proteins are then resuspended in a relatively small volume of isotonic solution, preferably normal saline, and exhaustively dialyzed against a relatively large volume of isotonic solution. The dialysis substep effectively reduces the concentration of disinfectant as well as precipitating agent to a negligible level. If desired, the dialysis substep may be replaced by high speed centrifugation using conventional techniques for separating the proteins.

When practicing the present invention for disinfecting tissue products, the same general techniques which apply for blood product are applicable. A particularly suitable tissue product is corneas intended for transplanting to possible recipients with diseased or otherwise nonfunctional corneas.

It is also within the scope of the present invention to combine isotonic diluents. This is particularly applicable when disinfecting red blood cells because commercial collective units of red blood cells are frequently stored in anti-coagulant components which are isotonic, e.g., ACD (acid, citrate, dextrose), CPD (citrate, phosphate, dextrose), CPD-A (CPD and adenine). When sterilizing collective units of red blood cells stored in the above mentioned anti-coagulant isotonic solutions, the disinfectant composition may be prepared in a different isotonic diluent, e.g., normal saline, and combined with the anti-coagulant solution.

The method of this invention may be practiced by assembling the various chemical ingredients in any of a great number of sequences. Thus, for example, the diluent solute may be premixed with disinfectant for commercial packaging, and this pre-mixture then diluted with distilled, sterile water at the point of use.

The primary controlling considerations in these various possible sequences is that upon addition of diluent water, the resulting mixture is substantially isotonic with blood or exerts an osmotic pressure sufficient to prevent cell lysis. Aside from considerations of commercial practicality, the particular sequence employed is, by and large, immaterial to the practice of this invention.

Suitable disinfecting times will become apparent when considering the detailed examples which follow. It is understood that the disinfection time may be adjusted in accordance with well-known principles of chemistry to accommodate treatment of the tissue while it is refrigerated, or even while it is heated. Again, care must be taken in using such lower or higher temperatures to avoid damage to the tissue from the temperature exposure itself—or from the combination of conditions of temperature and disinfecting substance.

Practicing this invention procedure is practical, useful, streamlined and economical. Its advantages particularly include eliminating transmission of viruses and micro-organisms in blood transfusions and tissue transplants.

In particular, it is verified that the disinfecting process leaves substantially intact certain substances that are present in blood and are recognized as indicators of normal or healthy blood constituent activity. These verifications will be described in a later section of this document. In short, the method of the present invention disinfects blood constituents without damaging them.

All of the foregoing operational principles and advantages of the present invention will be more fully appreciated upon consideration of the following detailed examples.

EXAMPLE 1

The following describes a generalized procedure for sterilizing blood products.

Sterilization Technique—Certain constituents of human blood are disinfected as follows. First, if desired, the cellular blood constituents may be separated from the plasma and from plasma fractions or proteins such as coagulating factors, globulins and so forth.

If this is not done, however, there is no effect on the particular constituents of interest. Moreover, with the refinements of the invention described herein, it is possible to preserve the other fractions (with or without disinfecting them) through the disinfection process.

Next, the blood product containing the constituents of interest is exposed for a suitable time to a disinfectant compositions. The disinfectant composition may be prepared in any of a great range of concentrations and in a variety of ways. The disinfectant composition is isotonic with respect to red blood cells.

In standard procedure for collection and storage of red blood cells, the cells are first separated from whole blood by centrifugation and then may be washed in an isotonic solution. Since in such a procedure the cells may be in an isotonic solution already, one convenient way of practicing my invention for red blood cells may be to simply add the disinfectant solution in a relatively concentrated form to the mixture of red cells and isotonic solution as washing begins.

Such addition should be performed gradually, and while the red cells and isotonic solution are mixed. These precautions should be adequate to minimize exposure of any small portion of the cells to a large quantity of the disinfectant, and to ensure adequate uniform exposure of all cells to disinfectant.

Another possibility for red blood cells is to follow the usual washing procedure, except for the substitution of the disinfectant and isotonic solution for the isotonic solution alone. In either event, the disinfection can be performed either while the cells are in their original collection bag suspended in CPD or CPDA-1 or other anticoagulant, or in a larger bag or other container; or in a red blood cell bag containing ADSOL ® or other RBC preservative solution such as AS-1.

It is desirable to use a larger bag, so that the volume of disinfectant is less than half that of the bag, and the total volume of disinfectant and cells is substantially less than the total volume of the bag. The point here is simply to allow ample excess volume for thorough and effective mixing, so that none of the cells is overexposed and all are adequately exposed to the disinfectant.

Platelets, by contrast, are not usually washed in the present standard procedures for blood treatment. For present purposes, however, they are advantageously washed using any of the procedures described above for red blood cells.

Procedures for treatment and segregation of plasma proteins have been set forth above. General procedures for treatment of corneal and scleral tissue have also been outlined but, as will be understood, the disinfection arrangements must be accommodated to the special needs and circumstances of the harvesting, nutritive and surgical environment.

Following exposure of the blood product to the disinfectant, the disinfectant is removed from the subject constituent. Such removal advantageously includes washing, with or without the aid of automation. An automated cell washer (such as a COBE cell washer) may be used to particular advantage for red blood cells or for platelets.

The washer may be programmed to mix the disinfectant with the constituent for a few seconds, or for a few minutes. The washer may also be programmed to then wash the constituent automatically.

Automation increases the utility of the invention, since through the use of automation red blood cells, platelets, and even plasma proteins, may be washed rapidly and the invention practiced on a production scale. Disinfectant composition, as well as disinfection times, may be varied without departing from the scope and spirit of the invention.

EXAMPLE 2

The following example describes a procedure and disinfectant composition utilized to disinfect corneas.

Two corneas were immersed in a 1:200 dilution of a commercial chlorine dioxide liberating disinfectant available from ALCIDE. The diluent consisted of a normal saline solution (0.9% sodium chloride). The corneas were allowed to remain in the disinfectant composition for 30 seconds. The corneas were then washed 3 times in three different bottles of normal saline and subsequently examined by a slit lamp. There was no significant change, as evidenced by an epithelium layer which was intact with no damage and a stroma which was clear with no edema. The endothelium showed no change in size or shape.

EXAMPLE 3

The following example describes a procedure for disinfecting red blood cells with a pyruvic acid and sodium chlorite disinfectant with a 0.45% sodium chloride diluent.

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous pyruvic acid solution was added to 30 mL of 0.45% aqueous sodium chloride. Then 3 mL of a 2.73% aqueous sodium chlorite solution was added to the pyruvic acid in 0.45% sodium chloride solution. The disinfectant composition was allowed to sit at room temperature for 75 minutes and then it was diluted 1:10 in 0.45% aqueous sodium chloride. The resulting disinfectant composition is 0.125% pyruvic acid and 0.23% sodium chlorite.

Three mL of packed red blood cells which were separated from the whole blood during the centrifugation was mixed with 3 mL of the disinfectant composition. The red blood cell and disinfectant composition mixture was allowed to incubate for 2 minutes.

Following the incubation step the red blood cells were again centrigued and washed four times with equal volume of 0.45% sodium chloride.

A control sample was treated by adding 3 mL of packed red blood cells to 3 mL of 0.45% sodium chloride aqueous solution (½ normal saline) and incubating for two minutes at room temperature. The control red blood cells and 0.45% sodium chloride mixture was centrifuged and washed in the same manner as the test sample.

Results indicated that there was no hemolysis of the disinfectant composition treated red blood cells as evidenced by the supernatants. Furthermore, standard Wright stain slides of the red blood cells treated with the disinfectant composition showed normal red blood cell morphology and no red blood cell fragments were seen. An interpretation of these results indicates that pyruvic acid-sodium chlorite in 0.45% sodium chloride (½ normal saline) causes no hemolysis or deformation of red blood cells.

EXAMPLE 4

The following example describes a procedure for disinfecting red blood cells with a lactic acid and sodium chlorite disinfectant in aqueous 0.45% sodium chloride (½ normal saline).

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous lactic acid solution was added to 30 mL of 0.45% aqueous sodium chloride. Then 3 mL of a 2.73% aqueous sodium chlorite solution was added to the lactic acid in 0.45% sodium chloride solution. The disinfectant composition was allowed to sit at room temperature for 75 minutes and then it was diluted 1:10 in 0.45% aqueous sodium chloride. The resulting disinfectant composition is 0.125% lactic acid and 0.23% sodium chlorite.

Three mL of packed red blood cells which were separated from the whole blood during the centrifugation was mixed with 3 mL of the disinfectant composition. The red blood cell and disinfectant composition mixture was allowed to incubate for 2 minutes.

Following the incubation step the red blood cells were again centrigued and washed four times with equal volume of 0.45% sodium chloride.

A control sample was treated by adding 3 mL of packed red blood cells to 3 mL of 0.45% aqueous sodium chloride solution (½ normal saline) and incubating for two minutes at room temperature. The control red blood cells and 0.45% sodium chloride mixture was centrifuged and washed in the same manner as the test sample.

Results indicated that there was no hemolysis of the disinfectant composition treated red blood cells as evidenced by the supernatants. Furthermore, standard Wright stain slides of the red blood cells treated with the disinfectant composition showed normal red blood cell morphology and no red blood cell fragments were seen. An interpretation of these results indicates that lactic acid-sodium chlorite in 0.45% sodium chloride (½ normal saline) causes no hemolysis or deformation of red blood cells.

EXAMPLE 5

The following example describes a procedure for disinfecting red blood cells with a lactic acid and sodium chlorite disinfectant with 5% aqueous dextrose Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous lactic acid solution was added to 30 mL of 5% aqueous dextrose. Then 3 mL of a 2.73% aqueous sodium chlorite solution was added to the lactic acid in 5% aqueous dextrose. The disinfectant composition was allowed to sit at room temperature for 75 minutes and then it was diluted 1:10 in 5% aqueous dextrose. The resulting disinfectant composition is 0.125% lactic acid and 0.23% sodium chlorite.

Three mL of packed red blood cells which were separated from the whole blood during the centrifugation was mixed with 3 mL of the disinfectant composition. The red blood cell and disinfectant composition mixture was allowed to incubate for 2 minutes.

Following the incubation step the red blood cells were again centrigued and washed four times with equal volume of 0.45% sodium chloride.

A control sample was treated by adding 3 mL of packed red blood cells to 3 mL of 5% aqueous dextrose solution and incubating for two minutes at room temperature. The control red blood cells and 5% aqueous dextrose mixture was centrifuged and washed in the same manner as the test sample.

Results indicated that there was no hemolysis of the disinfectant composition treated red blood cells as evidenced by the supernatants. Furthermore, standard Wright stain slides of the red blood cells treated with the disinfectant composition showed normal red blood cell morphology and no red blood cell fragments were seen. An interpretation of these results indicates that lactic acid-sodium chlorite in 5% aqueous dextrose causes no hemolysis or deformation of red blood cells.

EXAMPLE 6

The following example describes a procedure for disinfecting red blood cells with a pyruvic acid and sodium chlorite disinfectant with a 5% aqueous dextrose diluent.

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous pyruvic acid solution was added to 30 mL of 5% aqueous dextrose. Then 3 mL of a 2.73% aqueous sodium chlorite solution was added to the pyruvic acid in 5% aqueous dextrose. The disinfectant composition was allowed to sit at room temperature for 75 minutes and then it was diluted 1:200 in 5% aqueous dextrose. The resulting disinfectant composition is 0.006% pyruvic acid and 0.011% sodium chlorite.

Three mL of packed red blood cells which were separated from the whole blood during the centrifugation was mixed with 3 mL of the disinfectant composition. The red blood cell and disinfectant composition mixture was allowed to incubate for 10 minutes.

Following the incubation step the red blood cells were again centrigued and washed with 2 mL of 5% dextrose solution. The supernatant from this wash was observed for signs of hemolysis.

A control disinfectant solution was prepared in the same manner as the disinfectant solution described above except that all dilutions were performed with distilled water instead of 5% dextrose. A control sample was treated by adding 3 mL of packed red blood cells to 3 mL of the control disinfectant solution. The control sample was also incubated for 10 minutes at room temperature and then centrifuged and washed in the same manner as the test sample.

Results indicated that there was no hemolysis of the red blood cells treated with the disinfectant composition in 5% dextrose diluent as evidenced by the supernatants. In contrast, red blood cells treated the control disinfectant composition in distilled water showed massive hemolysis.

Furthermore, standard Wright stain slides of the red blood cells treated with the disinfectant composition in 5% dextrose showed normal red blood cell morphology and no red blood cell fragments were seen. Control red blood cells were almost totally destroyed and did not retain Wright stain.

An interpretation of these results indicates that pyruvic acid-sodium chlorite in 5% dextrose causes no hemolysis or deformation of red blood cells.

EXAMPLE 7

The following example describes a procedure for disinfecting red blood cells with a succinic acid and sodium chlorite disinfectant with a 0.45% sodium chloride diluent.

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous succinic acid solution was added to 30 mL of 0.45% aqueous sodium chloride. Then 3 mL of a 2.73% aqueous sodium chlorite solution was added to the succinic acid in 0.45% sodium chloride solution. The disinfectant composition was allowed to sit at room temperature for 75 minutes and then it was diluted 1:10 in 0.45% aqueous sodium chloride. The resulting disinfectant composition is 0.125% succinic acid and 0.23% sodium chlorite.

Three mL of packed red blood cells which were separated from the whole blood during the centrifugation was mixed with 3 mL of the disinfectant composition. The red blood cell and disinfectant composition mixture was allowed to incubate for 2 minutes.

Following the incubation step the red blood cells were again centrigued and washed four times with equal volume of 0.45% sodium chloride.

A control sample was treated by adding 3 mL of packed red blood cells to 3 mL of 0.45% sodium chloride aqueous solution (½ normal saline) and incubating for two minutes at room temperature. The control red blood cells and 0.45% sodium chloride mixture was centrifuged and washed in the same manner as the test sample.

Results indicated that there was nc hemolysis of the disinfectant composition treated red blood cells as evidenced by the supernatants. Furthermore, standard Wright stain slides of the red blood cells treated with the disinfectant composition showed normal red blood cell morphology and no red blood cell fragments were seen. An interpretation of these results indicates that succinic acid-sodium chlorite in 0.45% sodium chloride (½ normal saline) causes no hemolysis or deformation of red blood cells.

EXAMPLE 8

The following example describes a procedure for disinfecting red blood cells with a citric acid and sodium chlorite disinfectant with a 0.45% sodium chloride diluent.

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous citric acid solution was added to 30 mL of 0.45% aqueous sodium chloride. Then 3 mL of a 2.73% aqueous sodium chlorite solution was added to the citric acid in 0.45% sodium chloride solution. The disinfectant composition was allowed to sit at room temperature for 75 minutes and then it was diluted 1:10 in 0.45% aqueous sodium chloride. The resulting disinfectant composition is 0.125% citric acid and 0.23% sodium chlorite.

Three mL of packed red blood cells which were separated from the whole blood during the centrifugation was mixed with 3 mL of the disinfectant composition. The red blood cell and disinfectant composition mixture was allowed to incubate for 2 minutes.

Following the incubation step the red blood cells were again centrigued and washed four times with equal volume of 0.45% sodium chloride.

A control sample was treated by adding 3 mL of packed red blood cells to 3 mL of 0.45% sodium chloride aqueous solution (½ normal saline) and incubating for two minutes at room temperature. The control red blood cells and 0.45% sodium chloride mixture was centrifuged and washed in the same manner as the test sample.

Results indicated that there was no hemolysis of the disinfectant composition treated red blood cells as evidenced by the supernatants. Furthermore, standard Wright stain slides of the red blood cells treated with the disinfectant composition showed normal red blood cell morphology and no red blood cell fragments were seen. An interpretation of these results indicates that citric acid-sodium chlorite in 0.45% sodium chloride (½ normal saline) causes no hemolysis or deformation of red blood cells.

EXAMPLE 9

The following example describes a procedure for disinfecting red blood cells with a citric acid and sodium chlorite disinfectant with a 5% aqueous dextrose diluent.

Twenty mL of fresh peripheral blood from healthy donors was introduced into a heparinized tube. The blood was centrifuged at 2,000 rpm to separate the red blood cells.

A disinfectant composition was prepared using the following procedure:

Three mL of a 15% aqueous citric acid solution was added to 30 mL of 5% aqueous dextrose. Then 3 mL of a 2.73% aqueous sodium chlorite solution was added to the citric acid in 5% dextrose solution. The disinfectant composition was allowed to sit at room temperature for 75 minutes and then it was diluted 1:10 in 5% aqueous dextrose. The resulting disinfectant composition is 0.125% citric acid and 0.23% sodium chlorite.

Three mL of packed red blood cells which were separated from the whole blood during the centrifugation was mixed with 3 mL of the disinfectant composition. The red blood cell and disinfectant composition mixture was allowed to incubate for 2 minutes.

Following the incubation step the red blood cells were again centrifuged and washed four times with equal volume of 0.45% sodium chloride.

A control sample was treated by adding 3 mL of packed red blood cells to 3 mL of 5% aqueous dextrose solution and incubating for two minutes at room temperature. The control red blood cells sample was centrifuged and washed in the same manner as the test sample.

Results indicated that there was no hemolysis of the disinfectant composition treated red blood cells as evidenced by the supernatants. Furthermore, standard Wright stain slides of the red blood cells treated with the disinfectant composition showed norma red blood cell morphology and no red blood cell fragments were seen. An interpretation of these results indicates that citric acid-sodium chlorite in 5% aqueous dextrose causes no hemolysis or deformation of red blood cells.

Having thus described preferred exemplary embodiments of the present invention, it should le noted by those skilled in the art that the disclosures herein are exemplary only and that alternatives, adaptations and modifications may be made within the scope of the present invention. Accordingly, the present invention is not limited to the specific embodiments illustrated herein.

I claim:

1. A method for treating blood products and tissue products to inactivate viruses and microorganisms contained therein, said method comprising the steps of:
   mixing a blood product or a tissue product with a
       disinfectant composition for a sufficient time to inactivate said viruses, said disinfectant composition comprising:
a disinfectant selected from the group consisting of sodium chlorite and an acid, a water soluble chlorine dioxide liberating compound and an acid, and chlorine dioxide, and
an aqueous diluent, said diluent consisting essentially of water and a solute which, when the solute is at the proper concentration, the disinfectant composition is substantially isotonic with blood; and
separating the disinfectant from the blood product or tissue product, said blood product or tissue product being substantially viable for diagnostic or therapeutic use.

2. The method according to claim 1 wherein said blood product is red blood cells.

3. The method according to claim 1 wherein said tissue product is corneas.

4. The method according to claim 1 wherein said acid is an inorganic acid selected from the group consisting of hydrochloric acid, sulfuric acid, and phosphoric acid.

5. The method according to claim 1 wherein said acid is an organic acid.

6. The method according to claim 1 wherein said organic acid is selected from the group consisting of lactic acid, acetic acid citric acid, sorbic acid, fumaric acid, succinic acid and pyruvic acid.

7. The method according to claim 1 wherein said solute is selected from the group consisting of saline, glucose, adenine, salts of alkali earth metals, dextrans, albumin, and saline-mannitol-dextrose-adenine.

8. The method according to claim 1 wherein said disinfectant composition further contains one or more additives selected from the group consisting of adenine, and inosine.

9. The method according to claim 2 wherein said mixing step and said separating step is performed with an automatic or semi-automatic cell washer.

10. The method according to claim 9 wherein said separating step comprises washing said red blood cells with a solution substantially isotonic with blood until the disinfectant is substantially removed.

11. The method according to claim 1 wherein said blood product contains plasma proteins and said separating step further comprises the step of precipitating the plasma proteins with a precipitating agent.

12. The method according to claim 11 wherein said precipitating agent is ammonium sulfate.

13. The method according to claim 11 further comprising the steps of resuspending the plasma proteins in an isotonic solution; and
dialyzing the suspended plasma proteins at a semipermeable membrane against an isotonic solution.

14. A method for treating red blood cells to inactivate viruses contained therein, said method comprising the steps of:
mixing said red blood cells with a disinfectant composition for a sufficient time to inactivate said viruses, said disinfectant composition comprising:
a sufficient amount of a disinfectant to inactivate said virus, said disinfectant comprising sodium chlorite and an acid; and
a diluent, said diluent consisting essentially of water and a solute which, when the solute is at the proper concentration, the disinfectant composition is substantially isotonic with blood; and
separating the disinfectant from the red blood cells, said red blood cells being substantially viable for diagnostic or therapeutic use.

15. The method according to claim 14 wherein said solute is selected from the group consisting of saline, glucose, adenine, salts of alkali earth metals, dextrans, albumin, and saline-mannitol-dextrose-adenine.

16. The method according to claim 14 wherein the disinfecting composition further contains one or more additives selected from the group consisting of adenine, and inosine.

17. The method according to claim 14 wherein the mixing step and separating step is performed with an automatic or semi-automatic cell washer.

18. The method according to claim 14 wherein the separating step consists of washing the red blood cells and disinfectant composition with a solution substantially isotonic with blood until the disinfectant is substantially removed.

19. The method according to claim 14 wherein said acid is an organic carboxylic acid.

20. The method according to claim 19 wherein said carboxylic acid is selected from the group consisting of acetic acid, citric acid, sorbic acid, lactic acid, fumaric acid, pyruvic acid, and succinic acid.

21. The method according to claim 14 wherein said acid is an inorganic acid selected from the group consisting of hydrochloric acid, sulfuric acid, and phosphoric acid.

22. The method according to claim 14 wherein said sodium chlorite comprises from about 0.0001% to about 1% of said disinfectant composition.

23. The method according to claim 14 wherein said acid is an organic acid selected from the group consisting of lactic acid, citric acid, succinic acid, pyruvic acid and said acid comprises from about 0.1% to about 1% of said disinfectant composition.

24. The method according to claim 14 wherein said sufficient time is from several seconds to several minutes.

25. A method for treating red blood cells to inactivate the AIDS virus contained therein, said method comprising the steps of:
mixing the red blood cells with a disinfectant composition for a sufficient time to inactivate said AIDS virus, said disinfectant composition comprising:
a disinfectant selected from the group consisting of sodium chlorite and an acid, and
an aqueous diluent, said diluent consisting essentially of water and a solute which, when the solute is at the proper concentration, the disinfectant composition exerts an osmotic pressure sufficient to prevent the hemolysis of said red blood cells;
separating the disinfectant from said red blood cells, said red blood cells being substantially viable for diagnostic or therapeutic use.

26. The method according to claim 25 wherein said acid is an inorganic acid selected from the group consisting of hydrochloric acid, sulfuric acid, and phosphoric acid.

27. The method according to claim 25 wherein said acid is and organic acid selected from the group consisting of lactic acid, citric acid, acetic acid, succinic acid, sorbic acid, fumaric acid, and sorbic acid.

28. The method according to claim 25 wherein said solute is selected from the group consisting of saline, glucose, adenine, salts of alkali earth metals, dextrans, albumin, and saline-mannitol-dextrose-adenine.

29. The method according to claim 25 wherein said diluent is selected from the group of aqueous solutions isotonic with blood cells consisting of 0.9% normal saline and 5% dextrose.

30. The method according to claim 25 wherein said sufficient amount of disinfectant is from 0.25% wt % sodium chlorite, said acid is present at about 0.13 wt % and said diluent is selected from the group consisting of 0.45% aqueous sodium chloride and 5% aqueous dextrose solution.

31. The method according to claim 25 wherein said sufficient amount of disinfectant is about 0.013 wt %, said acid is present at about 0.006 wt % and said diluent is selected from the group consisting of 0.9% aqueous sodium chloride and 5% aqueous dextrose.

32. The method according to claim 25 wherein said sufficient time is from about 2 minutes to about 10 minutes.

* * * * *